United States Patent [19]

Wong

[11] 4,250,611
[45] Feb. 17, 1981

[54] PROCESS FOR MAKING DRUG DELIVERY DEVICE WITH RESERVOIR

[75] Inventor: Patrick S. Wong, Palo Alto, Calif.

[73] Assignee: Alza Corporation, Palo Alto, Calif.

[21] Appl. No.: 31,498

[22] Filed: Apr. 19, 1979

Related U.S. Application Data

[63] Continuation of Ser. No. 775,718, Mar. 3, 1977, abandoned.

[51] Int. Cl.³ .................. B23P 3/00; B23P 19/04
[52] U.S. Cl. ................................. 29/460; 53/467;
128/130; 141/329; 156/122
[58] Field of Search .................. 29/417, 428, 460;
53/409, 432, 433, 452, 474, 467; 128/130;
156/18, 155, 145, 122, 293, 294; 141/325, 326,
327, 329; 277/126

[56] References Cited

U.S. PATENT DOCUMENTS

| | | | |
|---|---|---|---|
| 3,545,439 | 12/1970 | Duncan | 128/130 |
| 3,660,192 | 5/1972 | Smith et al. | 277/226 UX |
| 3,948,262 | 4/1976 | Zaffaroni | 128/130 X |

*Primary Examiner*—Charlie T. Moon
*Attorney, Agent, or Firm*—Paul L. Sabatine; Thomas E. Ciotti; Edward L. Mandell

[57] ABSTRACT

An intravaginal contraceptive system for the pre-programmed, unattended delivery of an antifertility steroid is disclosed. The system comprises (a) an antifertility steroid, (b) a delivery module comprising a reservoir for storing the steroid in an amount for execution of the program, a rate controller which maintains the rate of steroid delivered in a contraceptive effective amount throughout the life of the system, an energy source for transferring steroid from the reservoir to the vagina, and a portal for releasing the steroid from the module to the vagina, (c) a platform which integrates the module into a unit sized, shaped and adapted for insertion and retention in a vagina, and (d) a contraceptive program which provides for the controlled release of steroid to produce an antifertility effect over a prolonged period of time.

10 Claims, 3 Drawing Figures

PROCESS FOR MAKING DRUG DELIVERY DEVICE WITH RESERVOIR

CROSS-REFERENCE TO RELATED APPLICATION

This application is a continuation of U.S. patent application Ser. No. 775,718 filed on Mar. 3, 1977, now abandoned.

FIELD OF THE INVENTION

This invention pertains to an intravaginal system. The system comprises an antifertility steroid, a delivery module, a platform and a contraceptive program that operates as a unit for delivering an effective amount of an antifertility steroid to the vagina of a fertile female. More specifically, the invention relates to an intravaginal contraceptive system manufactured from block copolymers of styrene and butadiene in the form of an intravaginal device for delivering an antifertility steroid.

BACKGROUND OF THE INVENTION

Vaginal devices for delivering a drug are known to the prior art. For example, U.S. Pat. No. 3,545,439 issued to Gordon W. Ducan discloses an intravaginal ring-shaped device that can be made of varying types of polymeric materials. The device is formed of a solid polymer containing drug that is released by diffusion to the vagina. The device optionally contains a tension spring for keeping it in the vagina. In U.S. Pat. No. 3,920,805 patentee Theodore J. Roseman discloses a solid, polymeric device that has a nonmedical central core and an encircling medicated coating of the polymer. The device releases drug by diffusion and in a preferred embodiment, the device is ring-shaped with a flat tensioning spring molded in the nonmedicated central core.

While the above-described devices are useful for certain applications, serious disadvantages are frequently associated with these devices that limit their use. For example, generally the polymers used by the prior art are thermoset polymers which require molding and curing fabrication procedures to form solid devices. These fabrication procedures tend to restrict the shape of the device, and the use of said polymers limits the amount of drug that can be loaded into the polymer and leads to a more rigid device. Those versed in the art will recognize that if vaginal devices can be provided made of materials that are essentially free from the above tribulations, such devices would be a valuable advancement in the art and a useful improvement.

OBJECTS OF THE INVENTION

Accordingly, it is an immediate object of this invention to provide an improved intravaginal delivery system for the controlled and continuous delivery of antifertility steroid over a prolonged period of time.

Yet another object of the invention is to provide an intravaginal system comprising materials easy to fabricate into systems and which materials can release antifertility steroids at meaningful rates over a prolonged period of time.

Yet still another object of the invention is to provide an intravaginal delivery system that is flexible, can have high steroid loading, and which system can deliver progestational and estrogenic steroids at a controlled and useful rate over prolonged periods of time.

Another object of the invention is to provide an intravaginal delivery system manufactured with vaginally compatible materials for releasing antifertility steroids over a prolonged period of time.

Other objects, features, aspects and advantages of the invention will be more apparent to those versed in the art from the following detailed specification, taken in conjunction with the accompanying claims.

SUMMARY OF THE INVENTION

This invention concerns an intravaginal system useful for delivering antifertility steroids. The system comprises a wall made of a block copolymer of styrene and butadiene surrounding a reservoir containing an inner liquid mass transfer conductor and an antifertility steroid. The wall and the carrier are permeable to the passage of steroid by diffusion, but the permeability of the wall to the passage of steroid is lower than through the carrier. Since the permeability through the wall is lower, passage through the wall is the rate determining step for releasing an effective amount of steroid from the operable system to the vagina.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by numbers. The terms appearing earlier in the specification and in the description of the drawings, as well as embodiments thereof, are further described elsewhere in the disclosure.

DETAILED DESCRIPTION OF THE DRAWINGS

Figure 1:
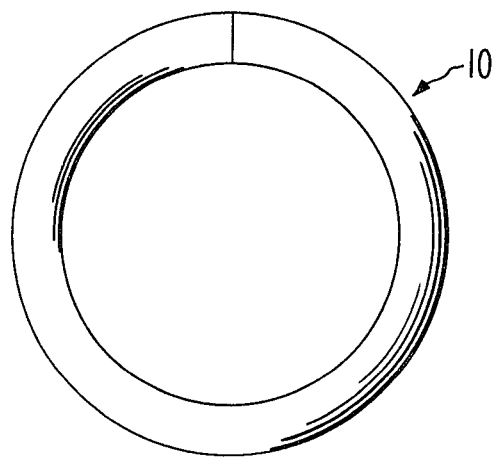
FIG. 1 illustrates an intravaginal system sized, shaped and adapted for insertion and retention in a vagina.

Turning now to the drawings in detail, which are examples of intravaginal contraceptives that can be used for releasing an antifertility hormone to the vagina for the management of contraception, and which examples are not to be construed as limiting the invention, one embodiment thereof is seen in FIG. 1 and identified by the numeral 10. The phrase "intravaginal contraceptive system" as used herein refers to a controlled dosage form which provides pre-programmed, unattended delivery of hormone, and for a time period, established to meet a specific contraceptive need.

Figure 2:
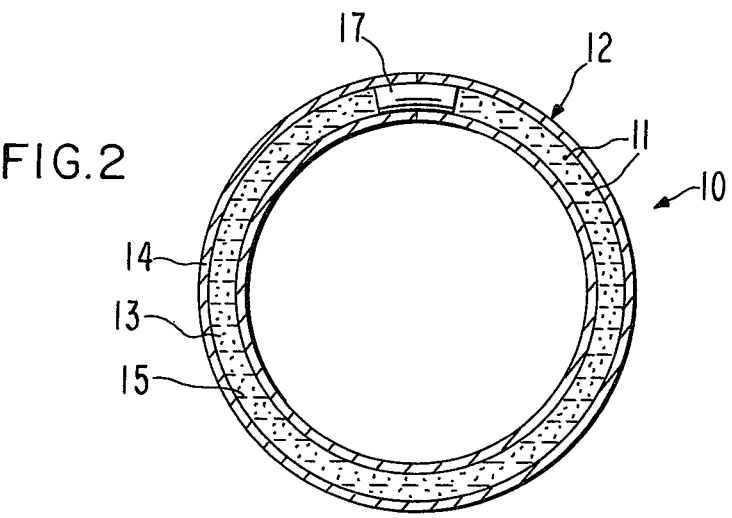
FIG. 2 illustrates the intravaginal system of FIG. 1 as seen in a cross-section, opened view and manufactured with an internal reservoir; and, FIG. 3 illustrates the intravaginal system of FIG. 1 in opened section showing means for filling the system.

System 10, as seen in FIG. 2, comprises an antifertility steroid 11, selected for producing a desired contraceptive effect when delivered to the target receptor site, the vagina, and a delivery module 12. Delivery module 12 is essentially the body of system 10 and it comprises (a) a reservoir 13 for storing an amount of hormone 11 required for execution of the prescribed contraceptive program, (b) a rate controller 14, or wall formed of a styrene-butadiene copolymer that maintains the prescribed rate of steroid administered throughout the life of system 10, (c) an energy source 11, or the concentration of steroid 11 in reservoir 13 that provides the driving means for transferring steroid 11 from a higher amount in reservoir 13 to rate controller 14, (d) an inner mass transfer conductor 15 for housing steroid 11 in reservoir 13, and (e) a portal 14 which in this invention is rate controller 14 that provides the exit from module 12 to the vagina.

System 10, comprising steroid 11 stored in module 12 which module 12, is integrated into a unit sized, shaped and adapted as a platform for placing in the vagina can embrace many shapes. That is, the platform can have various continuous, curved shapes, such as annular, or ring, oval, ellipse, toroidal, and the like. The novel antifertility system 10 can be used for delivering steroid 11 to animals, warm-blooded mammals including humans and primates, farm animals and laboratory animals. The dimensions of the system will vary depending on the host and the shape used for delivering the steroid. For example, at its maximum dimension the device will measure from one loci on the wall to a distant loci on the wall of from 0.4 cm to 12 cm, with presently preferred devices exemplified by an annular shaped system which can have an external diameter of from 0.5 cm to 16 cm, with general dimensions for various hosts as follows: humans 6 cm to 12 cm, sheep 2 cm to 7 cm, dogs 0.5 cm to 5.0 cm, swine 2 cm to 7.5 cm, household cats 0.4 cm to 4 cm and dairy cattle 5 cm to 12 cm.

DETAILED DESCRIPTION OF THE INVENTION

In accordance with the practice of this invention, it has now been unexpectedly found that certain vaginally acceptable block copolymers of styrene and butadiene can be used for forming rate controller 14 of intravaginal system 10 for the controlled release of steroid 11 by diffusion. The use of these materials is unexpected because the copolymer can be successfully used substantially free of any adverse affect on the vagina. The vagina is lined with an extremely delicate tissue and it is essential, therefore, that materials forming system 10 do not adversely effect the vagina. The copolymers used for the purpose of this invention are the vaginally compatible materials set forth below. By compatible is meant the materials are pharmaceutically acceptable within the environment of the vagina and generically to the host. That is, these materials do not break down in the vagina, there is no absorption of the materials and there is no deleterious action on the sensitive tissues in the area of the placement and retention of system 10 over a prolonged period of time.

The styrene-butadiene block copolymer useful for manufacturing rate controller 14 includes those generally formed by initiation at a chain end of an already formed polymeric chain. The block copolymers are thermo-plastic elastomers because of their ability to become fluid and moldable at elevated temperatures. These properties lend themselves to the manufacture of system 10. The block copolymer useful for the present purpose can be represented by the following general formula:

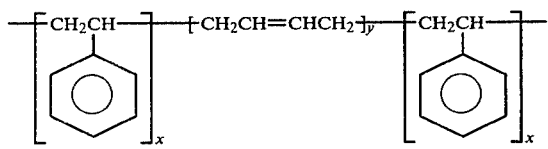

wherein x is $5 \times 10^1$ to $10 \times 10^4$ and y is $1 \times 10^3$ to $2 \times 10^4$. Generally, in a more preferred range the styrene block copolymer will have a molecular weight in the range of 10,000 to 20,000 and the butadiene will have a molecular weight in the range of 40,000 to 100,000. The styrene butadiene block copolymers suitable for the present purpose are permeable to antifertility effective amounts of progestational and estrogenic vaginally administrable steroids by diffusion, and these copolymers are known to the art and they can be synthesized according to the procedures disclosed in *Encyclopedia of Polymer Science and Technology*, Vol. 15, pages 508 to 530, 1971, published by Interscience Publishers, Inc., New York; *Polymers*, Vol. 17, 938 to 956, 1976; *Technical Bulletin* SCR-159, 1965, Shell Corp., New York; and references cited therein.

Exemplary inner mass transfer conductor 15 that are carriers suitable for housing steroid 11 in reservoir 13 are those liquid carriers permeable to the passage of both progestational and estrogenic steroids. These carriers include liquids capable of containing dissolved and undissolved steroid 11, and also capable of forming a liquid carrier wall interface at the inner surface of styrene butadiene wall 14. Typical carriers include a member selected from the group consisting of alkylene glycols, dialkylene glycols, poly(alkylene glycols), vegetable oils, animal oils, fruit oils, nut oils, marine oils, sylvan oils, inorganic oils, aqueous media such as water mixed with poly(alkylene glycols) including poly(ethylene glycols) having a molecular weight of 400 to 6000, poly(propylene glycol) having a molecular weight of 500 to 2000, glycerol polysorbate 80 and the like. Examples of carriers are known to the art in *Pharmaceutical Sciences*, by Remington, 1970, published by Mack Publishing Company, Easton Pa.

In the specification and the accompanying claims, the phrase "anti-fertility steroid" and the term "steroid" are used interchangeably and they broadly include progestational substances that have antifertility properties and estrogenic substances that have anti-fertility properties. These substances can be of naturally occurring or synthetic origin and they generally possess a cyclopentanophenanthrene nucleus. The term progestational substance as used herein embraces "progestogen" which term is used in the pharmaceutically acceptable steroid art to generically describe steroids possessing progestational activity, and the former also includes "progestins," a term widely used for synthetic steroids that have progestational effects. The active anti-fertility progestational agents that can be used to produce the desired effects in mammals, including humans, and primates, include without limitations: pregn-4-ene-3,20-dione, also known as progesterone; 19-nor-pregn-4-ene-3,20-dione; 17-hydroxy-19-nor-17α-pregn-5(10)-ene-20-yn-3-one; dl-11α-ethyl-17-ethynyl-17-α-hydroxygon-4-ene-3-one; 17 ethynyl 17-hydroxy-5(10)-estren-3-one; 17α-ethynyl-19-norestosterone;6-chloro-17-hydroxypregna-4,6-diene-3,20-dione; 17α-hydroxy-6α-methyl-17(-1-propynl-)androst-4-ene-3-one; 9α,10α-pregna-4,6-diene-3,20-dione; 17-hydroxy-17α-pregn-4-en-20-yne-3-one; 19-nor-17α-preg-4-en-20-yen-3,17-diol; 17-hydroxypregn-4-ene-3,20-dione; 17α-hydroxyprogesterone; 1-7-hydroxy-6α-methylpregn-4-ene-3,20-dione; mixtures thereof and the like.

The term estrogenic and estrogenic anti-fertility agents as used herein also includes the compounds known as estrogens that possess anti-fertility properties including α-estradiol, α-estradiol 3-benzoate, 17-α-cyclopentanepropionate estradiol, 1,3,5(10)-estratriene- 3,17α-diol dipropionate, estra-1,3,5(10)-triene 3,17-α-diol valerate, estrone, ethynyl estradiol, 17-ethinyl estradiol-3-methyl ether, 17-ethynyl estradiol-3-cyclopentoether, estriol, mixtures thereof, and the like. Generally, reservoir 13 will contain from 25 nanograms to 5 grams of progestational or estrogenic steroid for release at the rate of 0.05 micrograms to 50 milligrams per day, and in a presently preferred range of 0.5 milligrams to 6.0 milligrams per day to the uterus of an adult child bearing woman. Generally, the system can be used from a period of 1 day to 1 year, or longer.

Additionally, the above progestational and estrogenic agents can be in the form of their pharmacologically accepted derivatives, such as their hydroxy or keto groups can be in a derivative form for the present purpose. The progestational or estrogenic derivative used should easily convert to the parent agent upon its release from the device by biological activities such as enzymatic transformation, pH assisted hydrolysis in uteri, tissue and metabolism and the like. The derivative can also be used to control the solubility of the agent in the liquid core and to assist in metering the agent from the device. Suitable derivatives include without limitation, esters with pharmaceutically acceptable acids such as acetate, glucuronate, benzoate, propionate, butyrate, valeroate, hexanoate, heptanoate, maleate, citrate, succinate, tartrate, fumarate, malate, ascorbate, sulphate, phosphate and the like; ethers such as lower alkoxy-tetrahydropyran-yl, unsubstituted tetrahydropyran-yl, silyl moieties, trifluoromethyloxy, cyclopentyl enol ethers and other functional groups such as ureido, and the like.

Figure 3:
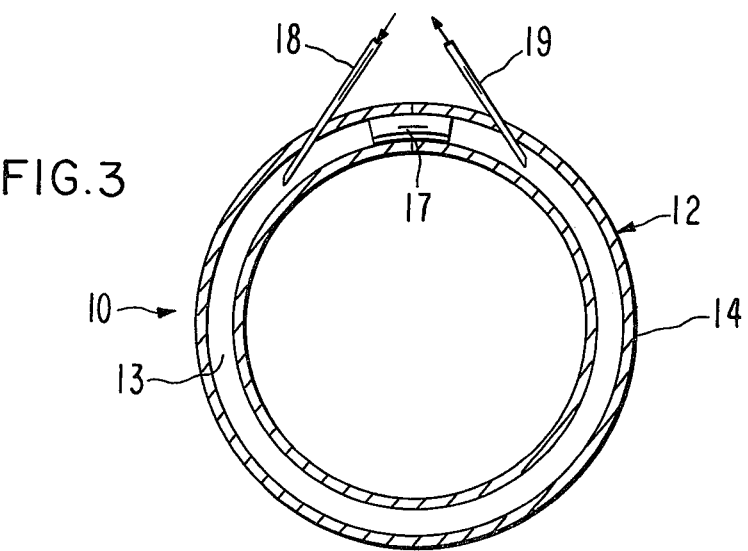

The intravaginal systems used for the purpose of this invention are manufactured as follows: First, a section of the above-described styrene butadiene block copolymer vaginal acceptable tubing was washed with water for 48 to 56 hours, and then dried in air at room temperature. Then, the tubing was cut into appropriate lengths and shaped like a ring, as seen in FIG. 3, and molded into a torus at 165° C. Next, a solid polymeric plug 17, having an outside diameter equivalent to the inside diameter of the tube was very lightly dampened with methylene chloride and inserted into the tube for joining the opened tube at its two ends, thereby forming a closed system. Then the hollow ring is filled by injecting a steroid carrier mixture into reservoir 13 through inlet port or needle 18 with continuous filling of reservoir 13 until all the air is displaced through outlet port or needle 19. This procedure completely fills reservoir 13. Finally, the needle punctures were sealed with a little methylene chloride. Reservoir 13 was filled with progesterone in polyethylene glycol having a molecular weight of 400, 50% wt/wt.

Additional systems 10 were prepared having a toroidal shape of the same copolymer with a wall 14 having a thickness of 1.78±0.08 mm, an internal diameter of 6 mm, an outside diameter of 4.4 cms, and a reservoir containint 35% progesterone and 65% polyethylene glycol having a molecular weight of 600; and a system of toroidal shape with a wall thickness of 2.79±0.08 mm containing in the reservoir 50% progesterone and 50% polyethylene glycol having a molecular weight of 600. The other dimensions were as previously described.

The delivery of steroids at meaningful rates from three systems made according to the mode of the invention was measured from three toroidal shaped systems. The results were as follows: (1) a system having a wall thickness of 2.79±0.08 mm and a progesterone loading of 0.7 gr had a steady state of release rate of 5.63±0.24 mg per day; (2) a system having a wall thickness of 1.78±0.08 mm and a progesterone loading of 1.3 gr had a steady state release rate of 9.49±0.25 mg per day; and (3) a system having a wall thickness of 0.75±0.08 mm and a norethindrone loading of 0.4 gr had a steady state release rate of 0.56±0.07 mg per day as measured over a prolonged period of 120 days.

The systems containing norethisterone were placed in the vagina of fertile women. The systems were comfortable and well-received by the vagina and the host. The systems are preferably placed between the rear endometrial wall of the vagina and the upper edge of the pubic bone. In this place, the medicating system releases a contraceptively effective amount of steroid over a prolonged period of 75 days to yield the intended effect.

It will be understood to those versed in the art in the light of the present specification, drawings and the accompanying claims that the invention makes available to the art both a novel and useful intrauterine system for delivering progestational and estrogenic steroids to produce a desired antifertility effect; and, the rate of release from these systems can be controlled to produce this effect, while simultaneously overcoming the problems associated with the prior art. It will be further understood to those versed in the art that different embodiments of this invention can be made without departing from the spirit and the scope of the invention. Accordingly, it is to be understood the invention is not to be construed as limited, but it embraces all equivalents inherent herein.

We claim:

1. A process for manufacturing a device for delivering a drug to a biological environment, which process comprises:
   (a) shaping a biocompatible tube to a shape and size adapted for placement in the environment;
   (b) inserting and sealing into one end of said tube a portion of solid polymeric plug;
   (c) forming a closed hollowed reservoir device by inserting and sealing the remaining portion of said plug into the other end of the tube;
   (d) positioning a drug inlet in the tube closely adjacent to the plug;
   (e) positioning an air outlet in the tube closely adjacent to the plug on the other side of the tube;
   (f) admitting a drug formulation through the inlet while venting air from the reservoir, and continuing such admittance until the reservoir is filled with formulation and the air has been displaced through the outlet; and,
   (g) removing the inlet and outlet and sealing the tube, thereby providing the device for delivering drug through the tube to the environment at a controlled rate over a prolonged period of time.

2. The process for manufacturing the device according to claim 1, wherein the biocompatible tube is a controller for maintaining the prescribed rate of drug delivered from the device over the prolonged period of time.

3. The process for manufacturing the device according to claim 1 wherein the drug formulation admitted into the reservoir comprises a drug and a mass transfer conductor for the drug.

4. The process for manufacturing the device according to claim 1 wherein the drug formulation admitted into the reservoir comprises a drug and a liquid carrier for the drug.

5. The process for manufacturing the device according to claim 1 wherein the biological environment is a vagina, and the device is sized and adapted for insertion and comfortable retention in the vagina.

6. The process for manufacturing the device according to claim 1 wherein the device is shaped like a ring.

7. The process for manufacturing the device according to claim 1 wherein the biological environment is a human.

8. The process for manufacturing the device according to claim 1 wherein the biocompatible tube is a thermoplastic polymer.

9. The process for manufacturing the device according to claim 1 wherein the biocompatible tube is shaped and then molded into said shape.

10. The process for manufacturing the device according to claim 1 wherein the solid polymeric plug has an outside diameter equivalent to the inside diameter of the biocompatible tube.

* * * * *